US005420262A

United States Patent [19]
Schmidt

[11] Patent Number: 5,420,262
[45] Date of Patent: May 30, 1995

[54] PROCESS FOR BLEACHING FATTY ALCOHOL ALKYL POLYGLYCOSIDE SOLUTIONS

[75] Inventor: Stefan Schmidt, Haltern, Germany

[73] Assignee: Huels Aktiengesellschaft, Marl, Germany

[21] Appl. No.: 104,898

[22] Filed: Aug. 12, 1993

[30] Foreign Application Priority Data

Oct. 10, 1992 [DE] Germany ............... 42 34 241.4

[51] Int. Cl.⁶ .............................................. C07H 1/06
[52] U.S. Cl. ............................. 536/18.5; 536/18.6; 536/124; 536/127
[58] Field of Search ............. 536/127, 18.6, 18.5, 536/124

[56] References Cited

U.S. PATENT DOCUMENTS

| | | | |
|---|---|---|---|
| 4,820,814 | 4/1989 | Lueders | 536/127 |
| 4,847,368 | 7/1989 | Lueders et al. | 536/18.6 |
| 4,866,156 | 9/1989 | Lüders | 536/18.6 |
| 4,898,934 | 2/1990 | Lueders et al. | 536/18.6 |
| 4,990,605 | 2/1991 | Lueders | 536/18.6 |
| 5,166,337 | 11/1992 | Ripke | 536/124 |
| 5,206,357 | 4/1993 | Schmidt | 536/18.6 |
| 5,212,292 | 5/1993 | Ripke | 536/18.6 |
| 5,234,554 | 8/1993 | Müller et al. | 203/89 |
| 5,266,690 | 11/1993 | McCurry, Jr. et al. | 536/127 |

FOREIGN PATENT DOCUMENTS 362671 4/1990 European Pat. Off. .
2-264789 10/1990 Japan .

Primary Examiner—David A. Redding
Assistant Examiner—Everett White
Attorney, Agent, or Firm—Oblon, Spivak, McClelland, Maier & Neustadt

[57] ABSTRACT

Fatty alcohol—alkyl polyglycoside solutions initially obtained in the preparation of alkyl polyglycosides are treated with alkali, temperature controlled and subsequently vacuum distilled. In this process, the fatty alcohol—alkyl polyglycoside solutions are first adjusted to a pH of 10 to 14 with alkali, after which their temperature is maintained at 60° to 120° C. for at least 2 hours. The fatty alcohol is then removed by distillation in vacuo at a reduced pH of 7 to 9.

12 Claims, No Drawings

PROCESS FOR BLEACHING FATTY ALCOHOL ALKYL POLYGLYCOSIDE SOLUTIONS

BACKGROUND OF THE INVENTION

1. Field of the Invention

The present invention provides a process for improving the color and the color stability of solutions containing $C_{8-24}$ fatty alcohols and $C_{8-24}$ alkyl polyglycosides by treating the solutions with alkali, maintaining the temperature of the treated solution for at least 2 hours, and finally distilling the treated solution to remove the fatty alcohol.

2. Discussion of the Background

Alkyl polyglycosides are non-toxic and easily degradable surfactants which are commonly used as detergents, cleaning agents, emulsifiers and dispersants. However, the desirable interfacial properties are only present if the alkyl groups of the polyglycosides have at least 8 C atoms.

Alkyl polyglycosides with long-chain alkyl groups are commonly prepared using one- or multi-step syntheses. For example, a two-step process is described in EP-A-0 306 652 which involves first glycosylating n-butanol and then transglycosylating the n-butyl glycoside with a long-chain alcohol. Unfortunately, after completion of the reaction, the alkyl polyglycoside product is present dissolved in the long-chain alcohol. To obtain a clear solution of the desired product, the long-chain alcohol must be removed.

A one-step preparation process is described, inter alia, in DE-A-4 101 252. Alternatively, EP-A-0 387 912 describes a one-step process in which long-chain fatty alcohols are first purified with alkali before they are reacted with glycosides under acidic catalysis. After neutralizing and distilling excess fatty alcohol from the reaction mixture, alkyl glycosides having improved color are obtained.

EP-A-0 132 046 describes a process in which an acidic reaction mixture containing glycosides and long-chain fatty alcohols is neutralized with an organic base, such as sodium methoxide, to a pH of 6.6 to 7. After distilling the fatty alcohol from the reaction mixture, alkyl glycosides having improved color are obtained.

Alkyl glycosides having long-chain alkyl groups can also be prepared in a one-step process as described in EP-A-0 362 671. After reacting a fatty alcohol with a glycoside, the reaction mixture is cooled to about 90° C., adjusted with alkali to at least pH 8, preferably to pH 8 to 10. After 30 minutes, the fatty alcohols are distilled from the alkaline solution. After a final bleaching step, light-colored, color-stable alkyl glycosides are obtained. Unfortunately, alkyl polyglycosides obtained by this process still do not have completely satisfactory color.

SUMMARY OF THE INVENTION

Accordingly, one object of the present invention is to improve the color and the color stability of alkyl polyglycosides.

The present inventors have found that this object can be achieved by adjusting the pH of the solution containing the fatty alcohols and alkyl polyglycosides, after completion of the reaction, to a pH of from 10 to 14, then maintaining the temperature of the treated solution at 60° to 120° C. for at least 2 hours before removing the fatty alcohol by distillation in vacuo at a pH of from 7 to 9.

DETAILED DESCRIPTION OF THE PREFERRED EMBODIMENTS

Suitable alkyl polyglycosides in accordance with the present invention can be obtained by continuous, batchwise, one- or multi-step processes. Preferably, the alkyl polyglycosides are prepared using a one step process. The formation of alkyl polyglycosides is suitably catalyzed under acidic conditions. Suitable acid catalysts useful in accordance with the process of the present invention include mineral acids, aliphatic and aromatic sulphonic acids or acidic ion exchangers.

Suitable glycosides useful in accordance with the process of the present invention include glucose, mannose, galactose or talose. Glucose is preferably used. Suitable alkyl polyglycosides have a degree of polymerization of from 1 to 5, preferably 1.1 to 1.4.

Suitable long-chain fatty alcohols which can be used in accordance with the present invention include octanol, decanol, dodecanol, tetradecanol and hexadecanol. The alkyl groups of the alkyl polyglycosides and those of the fatty alcohols preferably have 10 to 18 C atoms, preferably 12 to 16 C atoms.

The pH of the solution containing the fatty alcohols and the alkyl polyglycosides is suitably adjusted to an alkaline pH using aqueous or alcoholic solutions of alkali metal or alkaline earth metal hydroxides or alcoholic solutions of alkali metal alkoxides. The solution are preferably rendered alkaline using aqueous alkali metal hydroxides including sodium hydroxide, lithium hydroxide, or potassium hydroxide.

The addition of alkali preferably takes place at the temperature at which the alkyl polyglycosides are prepared (suitably 100°-120° C.), or at the temperature at which the solutions are to be maintained during the subsequent step suitably 60°-120° C.).

The pH of non-aqueous solutions containing the fatty alcohols and the alkyl polyglucosides is determined in samples diluted with water. If the PH of the solution is very high, precipitation can occur during the addition of alkali, which impairs the pumpability of the solutions; whereas, if the pH is too low the effect on the color of the products is too slight. Accordingly, the pH of the solution is adjusted to pH 10 to 14, preferably to pH 10 to 12.

The temperature of the alkaline solution is suitably maintained for at least 2 hours, typically from 3 to 48 hours, preferably 5 to 30 hours. During this time, the solution can be stirred, shaken or allowed to stand.

After the temperature of the alkaline solution has been maintained for a suitable time, the fatty alcohols are removed by distillation, preferably in a falling film apparatus, a thin layer evaporator, or a combination of both. The pH of the treated solution is reduced prior to distillation, preferably to pH 7 to 9.

The alkyl polyglycosides can be further treated by conventional bleaching methods as described in EP-A-0 362 671, the text of which is incorporated herein be reference.

The resulting products have very good color and color stability. 50% aqueous solutions have iodine color numbers of $\leq 15$. Moreover, the pH of aqueous solutions of these alkyl polyglycosides is stable.

Having generally described this invention, a further understanding can be obtained by reference to certain specific examples which are provided herein for purposes of illustration only and are not intended to be limiting unless otherwise specified.

EXAMPLES

The pH of the solutions was determined using a glass electrode. Samples were first diluted with isopropanol and water in the weight ratio 1:3:2.

Example 1

147.4 kg (750 mol) of a mixture of fatty alcohols (67% n-dodecanol, 27% n-tetradecanol, 6% n-hexadecanol) and 1.29 kg (6.8 mol) p-toluenesulphonic acid monohydrate were first combined to form a solution and 18 kg (100 mol) anhydrous glucose was subsequently added. The solution was reacted at 100° C./20 hPa in a 4 l stirring flask for 4 hours. The reaction mixture was cooled to 70° C. and adjusted to pH 11 using 25% aqueous NaOH. The temperature of the solution was then maintained at 70° C. for 24 hours. The solution was then adjusted to pH 9 using 25% aqueous NaOH.

A sample of this fatty alcohol—alkyl polyglycoside solution was stored at 60° C. After 12 hours, the pH was still at around 9.

After filtration, the solution was passed through a cascade of 3 thin layer evaporators (addition rate: 5 l/h, TLE 1: 100° C./100 hPa, TLE 2 and 3: 180° C./1 hPa). The remaining alkyl polyglycoside solution had a residual alcohol content of 2%. The iodine color number of this solution was around 7.

Example 2

1,970 g (10 mol) of a mixture of fatty alcohols (67% n-dodecanol, 27% tetradecanol, 6% n-hexadecanol) and 17.2 g (90 mmol) p-toluenesulphonic acid monohydrate were first combined together to form a solution and 240 g (1.3 mol) anhydrous dextrose was subsequently added. The solution was reacted at 100° C./20 hPa in a 4 l stirring flask for 4 hours. The reaction mixture was cooled to 70° C. and adjusted to pH 11 using 25% aqueous NaOH. The temperature of the solution was then maintained at 70° C. for 24 hours. The solution was then adjusted to pH 9 using 25% aqueous NaOH. After filtration, the fatty alcohol was removed by distillation in a rotary evaporator at 180° C./1 hPa.

The product was subsequently dissolved in water and treated at 80° C. and pH 7 with 3.5% hydrogen peroxide (based on the alkyl polyglycoside). The solution was stirred at 80° C. for 6 hours. The amount of water was chosen here such that after completion of the bleaching process a 50% aqueous solution resulted. After bleaching, the mixture had an iodine color number of 15.

Comparison Example A 169 kg (860 mol) of a mixture of fatty alcohols (67% n-dodecanol, 27% n-tetradecanol, 6% n-hexadecanol) and 1.57 kg (8.26 mol) p-toluenesulphonic acid monohydrate were first combined together to form a solution and 31 kg (172 mol) anhydrous dextrose was subsequently added. The solution was reacted at 100° C./15 hPa in a 250 l VA stirring vessel for 6 hours. The water of reaction was collected in a cold trap. The reaction mixture was cooled to 60° C. and adjusted to pH 11 using 25% aqueous NaOH.

After filtration, the solution was passed through a cascade of 3 thin layer evaporators (addition rate: 5 l/h, TLE 1: 100° C./100 hPa, TLE 2 and 3: 180° C./1 hPa). After a short time, severe loading and cracking occurred, so the distillation of the fatty alcohol had to be ended.

Comparison Example B 147.4 kg (750 mol) of a mixture of fatty alcohol (67% n-dodecanol, 27% n-tetradecanol, 6% n-hexadecanol), 18 kg (100 mol) anhydrous glucose, 520 g (5.1 mol) concentrated sulfuric acid and 450 g (4.25 mol) of sodium hypophosphite were reacted in the vessel of Comparison Example A and the mixture was then worked up as in Comparison Example A. The removal of the fatty alcohol in the thin layer evaporator cascade was again unsuccessful, since decomposition products were formed to a significant extent.

Comparison Example C (according to EP 0 362 671)

2,364 g (12 mol) of a mixture of fatty alcohols (67% n-dodecanol, 27% tetradecanol, 6% n-hexadecanol) and 4.96 g (26 mmol) p-toluenesulphonic acid monohydrate were first combined together to form a solution and 720 g (4 mol) anhydrous dextrose was subsequently added. The mixture was then reacted at 100° C./20 hPa in a 4 l stirring flask for 4 hours. After completion of the reaction, the pH was adjusted to 11 at 70° C. using 25% aqueous NaOH. The fatty alcohol was then immediately removed by distillation in a rotary evaporator at 180° C./1 hPa to such an extent that a solid having a residual fatty alcohol content of <2% resulted.

The product was bleached as indicated in Example 1. A 50% solution of the product had an iodine color number of 110.

What is claimed as new and desired to be secured by Letters Patent of the United States is:

1. A process for improving the color and color stability of a light colored solution of alkyl polyglycosides, consisting essentially of the steps of:
   treating an acidic solution consisting essentially of $C_{8-24}$ alkyl polyglycosides, acid and $C_{8-24}$ alkyl fatty alcohols with alkali to provide an alkaline solution;
   maintaining the temperature of said alkaline solution at 60° to 120° C. for at least two hours; and thereafter,
   distilling to remove said fatty alcohols in vacuo at a pH of from 7 to 9 to provide said solution of alkyl polyglycosides.

2. The process according to claim 1, wherein said acidic solution consists essentially of $C_{10-18}$ alkyl polyglycosides and $C_{10-18}$ alkyl fatty alcohols.

3. The process according to claim 2, wherein said acidic solution consists essentially of $C_{12-16}$ alkyl polyglycosides and $C_{12-16}$ alkyl fatty alcohols.

4. The process according to claim 1, wherein the pH of said acidic solution is adjusted to a pH of from 10 to 12 with said alkali.

5. The process according to claim 1, wherein the step of maintaining of the temperature of said alkaline solution is performed for from 3 to 48 hours.

6. The process according to claim 1, wherein the temperature of the step of maintaining of the temperature of said alkaline solution is at from 60° to 80° C.

7. A process for improving the color and color stability of a light colored solution of alkyl polyglycosides consisting of the steps of:
   treating an acidic solution consisting of $C_{8-24}$ alkyl polyglycosides, acid and $C_{8-24}$ alkyl fatty alcohols with alkali to provide an alkaline solution;

maintaining the temperature of said alkaline solution at 60°–120° C. for at least two hours; and thereafter, distilling to remove said fatty alcohols in vacuo at a pH of from 7 to 9 to provide said solution of alkyl polyglycosides.

8. The process according to claim 7, wherein said acidic solution consists of $C_{10-18}$ alkyl polyglycosides and $C_{10-18}$ alkyl fatty alcohols.

9. The process according to claim 8, wherein said acidic solution consists of $C_{12-16}$ alkyl polyglycosides and $C_{12-16}$ alkyl fatty alcohols.

10. The process according to claim 7, wherein the pH of said acidic solution is adjusted to a pH of from 10 to 12 with said alkali.

11. The process according to claim 7, wherein the step of maintaining the temperature of said alkaline solution is performed for from 3 to 48 hours.

12. The process according to claim 7, wherein the maintaining of the temperature of the step of maintaining the temperature of said alkaline solution is from 60° to 80° C.

* * * * *